(12) United States Patent
Garcia et al.

(10) Patent No.: US 7,923,707 B2
(45) Date of Patent: Apr. 12, 2011

(54) DISINFECTING DEVICE UTILIZING ULTRAVIOLET RADIATION

(75) Inventors: Ken V. Garcia, Williamson, NY (US); Carrie P. Garcia, Williamson, NY (US)

(73) Assignee: Oreck Holdings, LLC, Cheyenne, WY (US)

( * ) Notice: Subject to any disclaimer, the term of this patent is extended or adjusted under 35 U.S.C. 154(b) by 272 days.

(21) Appl. No.: 12/352,358

(22) Filed: Jan. 12, 2009

(65) Prior Publication Data

US 2009/0114854 A1    May 7, 2009

Related U.S. Application Data

(63) Continuation of application No. 11/360,046, filed on Feb. 22, 2006, now Pat. No. 7,476,885.

(51) Int. Cl.
*A61N 5/06* (2006.01)
*G02B 5/00* (2006.01)

(52) U.S. Cl. .................. 250/504 H; 250/504 R; 15/339

(58) Field of Classification Search .............. 250/504 R, 250/504 H, 365, 372, 393, 453.11, 454.11, 250/455.11, 461.1, 472.1, 473.1; 15/4, 5, 15/21.1, 41.1, 42, 43, 89, 90, 92, 105, 105.52, 15/184, 186–188, 313, 319, 339, 351, 340.1, 15/340.2, 340.3, 340.4; 422/22, 24, 186.3; 134/6–9, 21, 201
See application file for complete search history.

(56) References Cited

U.S. PATENT DOCUMENTS

| | | |
|---|---|---|
| 2,590,152 A | 3/1952 | Buckey |
| 3,798,704 A | 3/1974 | Kilstrom |
| 4,355,436 A | 10/1982 | Hertzberg |
| 4,498,214 A | 2/1985 | Oxel |
| 4,786,812 A | 11/1988 | Humphreys |
| 4,907,316 A | 3/1990 | Kurz |
| 5,014,387 A | 5/1991 | Hays |
| 5,045,118 A | 9/1991 | Mason et al. |
| 5,233,723 A | 8/1993 | Hung |
| 5,467,501 A | 11/1995 | Sepke |
| 5,968,455 A | 10/1999 | Brickley |
| 6,094,767 A | 8/2000 | Iimura |
| 6,239,442 B1 | 5/2001 | Iimura |
| 6,514,356 B2 | 2/2003 | Vystreil et al. |
| 6,572,711 B2 | 6/2003 | Sclafani et al. |
| 6,760,952 B1 | 7/2004 | Stegens |
| 6,776,824 B2 | 8/2004 | Wen |
| 6,968,587 B2 | 11/2005 | Grey |
| 7,013,521 B2 | 3/2006 | Grey |
| 7,444,711 B2 * | 11/2008 | Garcia et al. ............... 15/324 |
| 7,476,885 B2 * | 1/2009 | Garcia et al. ............. 250/504 H |
| 7,507,980 B2 * | 3/2009 | Garcia et al. ............. 250/504 R |

(Continued)

FOREIGN PATENT DOCUMENTS

DE    004138162 C1    9/1992

(Continued)

*Primary Examiner* — Bernard E Souw

(74) *Attorney, Agent, or Firm* — Winston & Strawn LLP

(57) ABSTRACT

A disinfecting device is presented having a UV light source for radiation of a cleaning medium to eradicate the medium of infestation agents such as molds, viruses, bacteria and dust mites. The device enhances the disinfection of the medium by providing mechanisms for enhanced penetration of the UV light into the cleaning medium. The device also offers enhanced heat dissipation to promote effective use of the device. Also provided are safety mechanisms to promote the safe and advantageous use of the UV device.

20 Claims, 15 Drawing Sheets

U.S. PATENT DOCUMENTS

| | | | |
|---|---|---|---|
| 7,721,383 B2 * | 5/2010 | Garcia et al. | 15/324 |
| 2001/0004719 A1 | 6/2001 | Sommer | |
| 2004/0077407 A1 | 4/2004 | Jandel | |
| 2004/0107528 A1 | 6/2004 | LeClear et al. | |
| 2004/0111826 A1 | 6/2004 | Grey | |
| 2004/0211444 A1 | 10/2004 | Taylor | |
| 2004/0221406 A1 | 11/2004 | Grey | |
| 2004/0244138 A1 | 12/2004 | Taylor | |
| 2004/0255411 A1 | 12/2004 | Grey | |
| 2005/0000543 A1 | 1/2005 | Taylor | |
| 2005/0010331 A1 | 1/2005 | Taylor | |
| 2005/0022844 A1 | 2/2005 | Field et al. | |
| 2006/0020369 A1 | 1/2006 | Taylor | |
| 2006/0216193 A1 | 9/2006 | Johnson et al. | 422/24 |
| 2006/0236496 A1 | 10/2006 | Oh et al. | |
| 2007/0192986 A1 | 8/2007 | Garcia et al. | |
| 2007/0192987 A1 | 8/2007 | Garcia et al. | |
| 2007/0194255 A1 | 8/2007 | Garcia et al. | |
| 2007/0209144 A1 | 9/2007 | Fester et al. | 15/339 |
| 2007/0209147 A1 | 9/2007 | Krebs et al. | |
| 2008/0061252 A1 | 3/2008 | Garcia et al. | |
| 2009/0184268 A1 * | 7/2009 | Garcia et al. | 250/504 R |

FOREIGN PATENT DOCUMENTS

| | | |
|---|---|---|
| DE | 004139199 | 6/1993 |
| JP | 2004-283545 | 10/2004 |

* cited by examiner

Fig. 14C
Fig. 14A
Fig. 14B
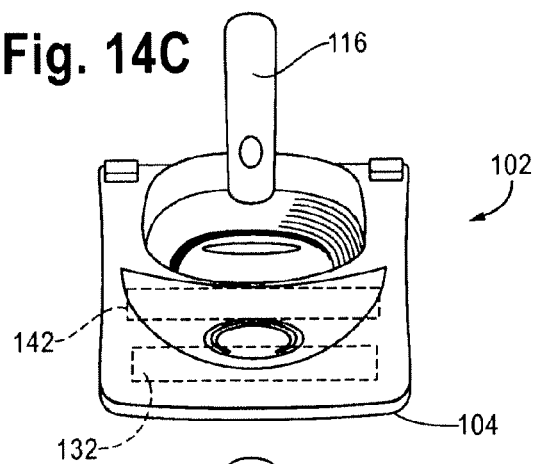
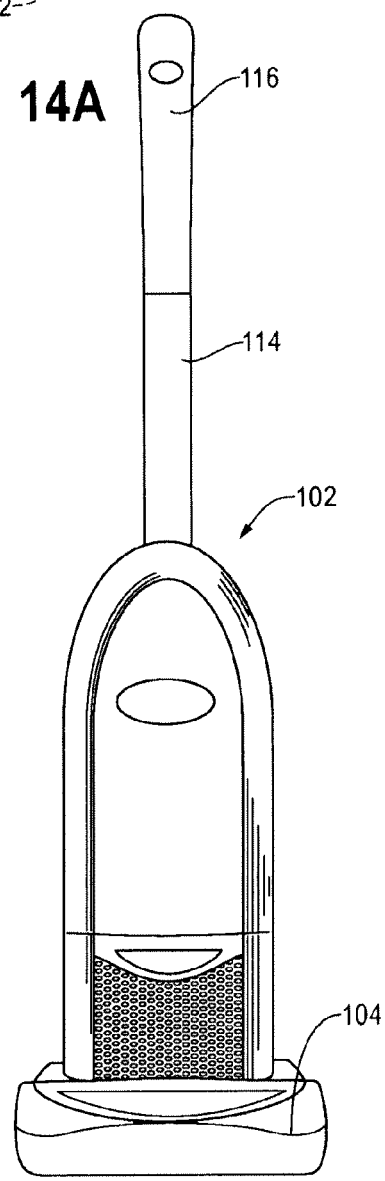
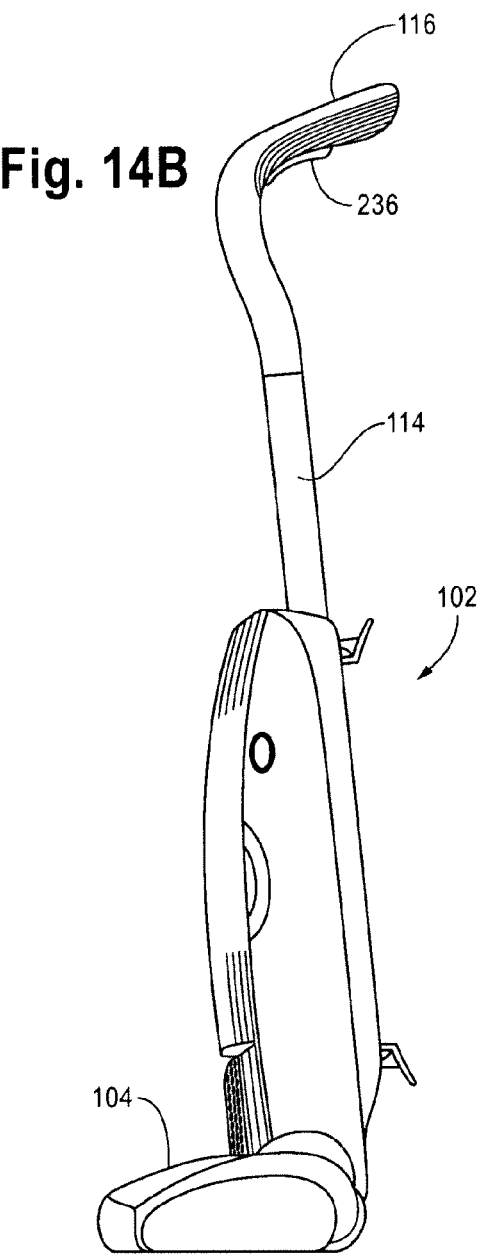

DISINFECTING DEVICE UTILIZING ULTRAVIOLET RADIATION

CROSS-REFERENCE TO RELATED APPLICATIONS

This application is a Continuation Application of U.S. patent application Ser. No. 11/360,046, filed Feb. 22, 2006, which will issue as U.S. Pat. No. 7,476,885 on Jan. 13, 2009.

STATEMENT REGARDING FEDERALLY SPONSORED RESEARCH OR DEVELOPMENT

None

REFERENCE TO MICROFICHE APPENDIX

Not applicable

TECHNICAL FIELD

1. Field of the Invention

The invention generally relates to using ultraviolet radiation to disinfect various cleaning media. The invention more particularly relates to devices and processes that can be employed to disinfect or sanitize infestation agents within various cleaning media by using ultraviolet radiation.

2. Background of the Invention

Many homes and businesses suffer from infestations of allergens and other undesirable organic and inorganic substances, such as molds, viruses, bacteria, and dust mites. Floor coverings such as carpeting in homes and hotels, for example, can contain a high concentration of organic or inorganic substances which create a potentially unhealthy or harmful environmental condition. A common indoor allergen in carpeting and mattresses that can trigger allergy symptoms in humans is the dust mite, a microscopic insect related to spiders. It has been claimed that allergies developed in the early years of a child's life due to exposure to allergens can result in life-long allergic responses or more serious medical conditions such as asthma. Exposure to mold spores, for example, has been linked to certain types of respiratory illnesses. Long-term exposure to mold may cause asthma or other respiratory problems, even in individuals who are not naturally sensitive or allergic to mold.

Conventional cleaning methods do not effectively reduce populations of infestation agents present within carpeting. Standard vacuum cleaners do not sanitize or disinfect carpeting, and vacuuming alone usually removes only a fraction of allergens from carpeting. Typically, steam cleaning is cumbersome, expensive, and may involve the use of chemicals. Also, steam cleaning can leave a carpet and its carpet pad in a wet condition that can support the undesirable growth of molds, mildew, bacteria, or dust mites in or beneath the carpet. As another alternative, chemical powders or dry carpet cleaning powders comprised primarily of chemical pesticides and insecticides may be used to clean carpeting. The potential health and safety hazards associated with such chemical powders, however, often outweigh any benefits that might be obtained by using them.

Many experts have suggested that the only solution to dealing with infestation agents in carpeting is to remove existing carpeting altogether and to refrain from using carpeting as a floor covering. However, for many individuals who find carpeting desirable, and for many applications where carpeting is an optimum choice for a floor covering, this is not an acceptable solution. As a result of the inadequacy of conventional carpet cleaning methods, however, carpeting in homes and commercial establishments can become an ideal environment in which dust mites, germs, bacteria, viruses, molds and other pathogens or microorganisms can live, grow, and multiply.

In addition, mattresses and other like articles are often afflicted by infestation agents. By the nature of how a mattress is used for rest or sleep, it is frequently in close contact with humans or animals that may shed dead skin, for example, or discard other organic substances that are retained in the mattress. Insects such as dust mites can thrive on this organic matter and quickly develop into a significant population within the mattress. As described above for carpeting, conventional cleaning methods applied to a mattress cannot both safely and effectively reduce populations of infestation agents present within the mattress.

It has been discovered that ultraviolet ("UV") light, particularly in the "C" spectrum ("UVC"), can deactivate the DNA of bacteria, viruses, germs, molds, and other pathogens and microorganisms, thus destroying their ability to reproduce and multiply. UVC light has been used effectively in various applications to disinfect and sanitize hospital rooms, medical clinics, food production facilities, and drinking water. However, existing products and processes have been unable to effectively and safely leverage the benefits of UV light to sanitize infestation agents in cleaning media such as carpeting and mattresses.

In view of the problems described above, safe and effective disinfecting devices are needed to address the deficiencies of conventional processes for sanitizing cleaning media such as carpeting and mattresses.

BRIEF DESCRIPTION OF THE FIGURES

The utility of the embodiments of the invention will be readily appreciated and understood from consideration of the following description of the embodiments of the invention when viewed in connection with the accompanying drawings.

FIG. 14A is a front elevational view of one embodiment of the device;

FIG. 14B is a side elevational view of one embodiment of the device; and

FIG. 14C is a top view of one embodiment of the device.

DETAILED DESCRIPTION OF PREFERRED EMBODIMENTS

The invention provides embodiments of cleaning and/or disinfecting devices, and features thereof, which offer various benefits: the devices maximize the disinfection capability of ultraviolet light ("UV light") by providing mechanisms for enhanced penetration of the UV light into a cleaning medium; the devices offer enhanced various heat dissipation and air flow engineering features that can promote and maintain the safe and advantageous use of UV light bulbs employed by the devices; and the devices may employ multiple and integrated safety mechanisms and systems that promote safe and effective use of the devices. As described below, embodiments of the invention can be applied effectively for disinfecting infestation agents which reside in cleaning media such as carpeting and mattresses. Cleaning operations such as vacuum cleaning operations, for example, can also be performed in association with certain embodiments of the devices described herein.

As applied herein, the term "cleaning medium" includes any area, region, substrate, surface, or other medium that can be acted upon by UV light. Examples of "cleaning media" include, without limitation, carpets, mattresses, furniture, drapery, or other surfaces or media (e.g., hardwood, linoleum, and ceramic tile). The cleaning medium can be horizontal, as in a typical floor or mattress top surface, or vertical or at any other angle, such as with drapery and furniture surfaces. The term "carpet" as used herein includes all floor coverings having fibers, whether looped, tufted, hooked, needlefelt, woven or of other design, indoor or outdoor, of natural or synthetic materials, wall-to-wall or roll goods.

The term "infestation agent" may include any organism, microorganism, contagion, pathogen, germ, insect, and/or any other organic or inorganic substance which can be affected by application of ultraviolet radiation, or which can be present on or within a cleaning medium. Examples of "infestation agents" include, without limitation, viruses, bacteria, dust mites, molds, roaches, fleas, bed bugs, spiders, and other insects.

With reference to FIGS. 1 through 4, various embodiments of the invention may be provided in association with a disinfecting device 102, which may be structured to combine the functional or structural features of a standard vacuum cleaner in conjunction with an ultraviolet light disinfecting apparatus. In certain embodiments, the device 102 may be structured for use as a combination cleaning and disinfecting device, in which both a disinfecting operation and a vacuum cleaning operation are performed by using the device 102. In various embodiments, the device 102 may be structured to perform disinfecting operations, with or without the additional capability to perform vacuum cleaning operations. Further, the device may be configured to selectively perform both disinfecting and vacuum cleaning operations or either operation independently.

Figure 1:
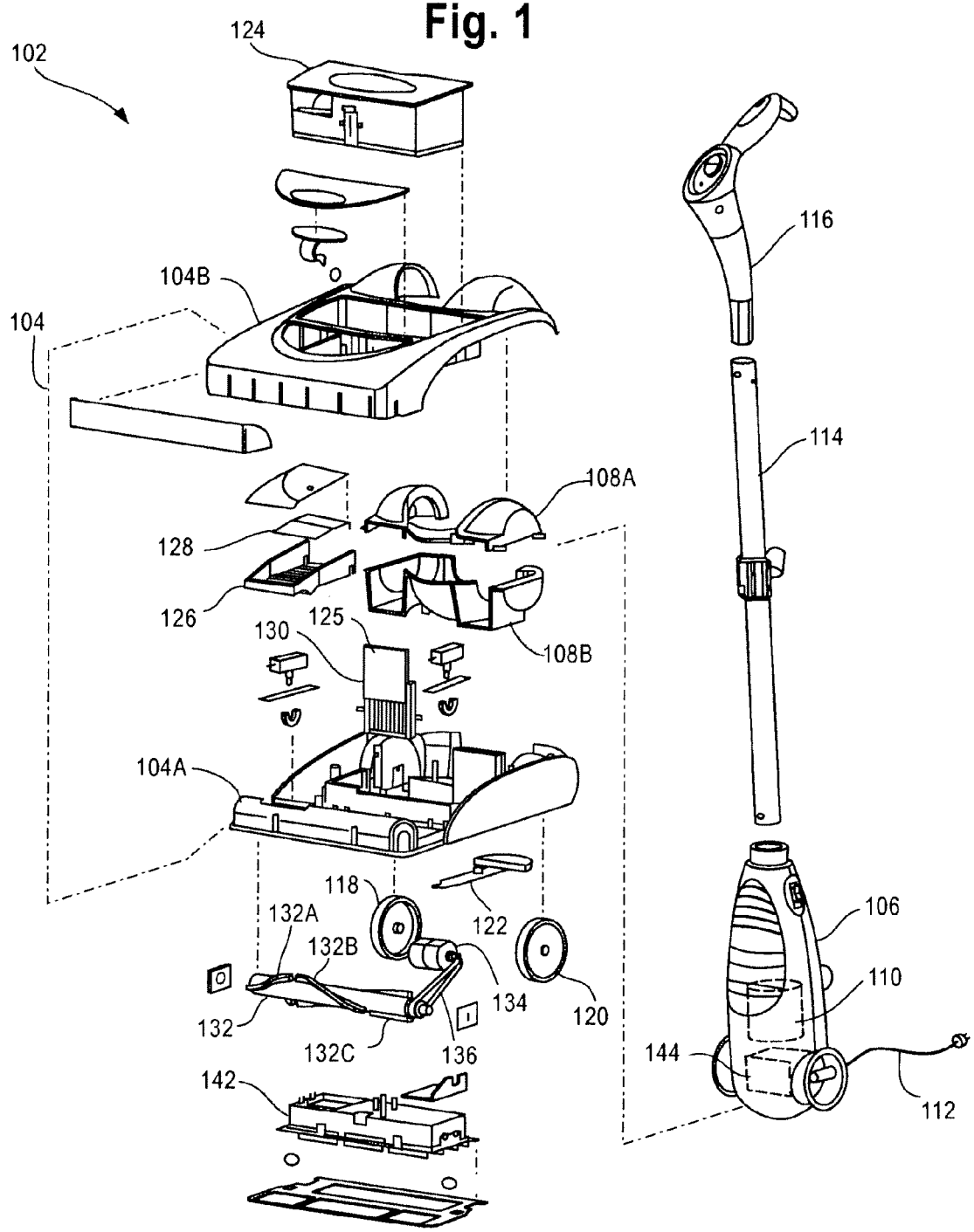
FIG. 1 is an exploded three-dimensional view of a disinfecting device structured in association with embodiments of the invention.

The device 102 includes a housing assembly 104 comprising a base 104A and a top 104B, which when connected together serve to house various components of the device 102. The housing assembly 104 may be operatively associated with a motor housing assembly 106 through interaction with a plenum cradle assembly 108, comprising a top plenum cradle 108A and bottom plenum cradle 108B, as shown in FIG. 1. The motor housing assembly 106 can contain a vacuum motor 110 designed to power the vacuum cleaning operations of the device 102. The motor 110 can be provided as an AC motor (e.g., 120 VAC) to power an impeller vane by direct drive to generate vacuum suction as needed by the device 102. Overall, the various electrical components of the device 102, including the motor 110, can be powered by a power cord 112 adapted to be received into an electrical outlet, for example, of a home or businesses, or another suitable external power source. In addition to or in place of external power sources, the device 102 may also be powered through the use of various battery pack systems known in the art. In certain embodiments, the device 102 may be configured to accept and use input power from a variety of 110-120 VAC/50-60 Hz external power sources. Alternately, the motor housing assembly 106 can be located within the housing assembly 104. The housing assembly 104 and motor housing assemblies, as well as other portions of the device, can take different configurations, such as the embodiment sown in FIGS. 14A-C, among others, without departing from the spirit of the invention.

It is envisioned that the device can be made in various configurations and sizes. For example, the device can be made in a hand-held embodiment and in various sizes for home or industrial use. Embodiments can be envisioned which accord use of various vacuum nozzle structures which incorporate the UV bulb assembly.

As shown in FIG. 1, a pole assembly 114 extends from the motor housing assembly 106 to a handle assembly 116 for the device 102. The handle assembly 116 of the device 102 may include various indicators (e.g., LED lights) that communicate the current operational condition of the device 102 to a user. The handle assembly can further include various switches that can be used to power the motor 110 or motors on or off, for example, and/or to activate or maintain other functions of the device 102, such as the UV bulb assembly, as described below.

The pole assembly 114 may be structured with multiple segments positioned in a telescoping configuration, to permit the pole assembly 114 to extend or contract in overall length. For example, the pole assembly 114 may be extended to an extended telescoping position (as shown in FIG. 1) for use on cleaning media such as carpeting or other floor surfaces. Also, the pole assembly 114 may be contracted in overall length to a contracted telescoping position to make overall handling of the device 102 more convenient and compact for applying the device 102 to cleaning media such as mattresses or furniture, for example, or to make the device 102 more compact for convenient storage during periods of non-use.

Figure 4:
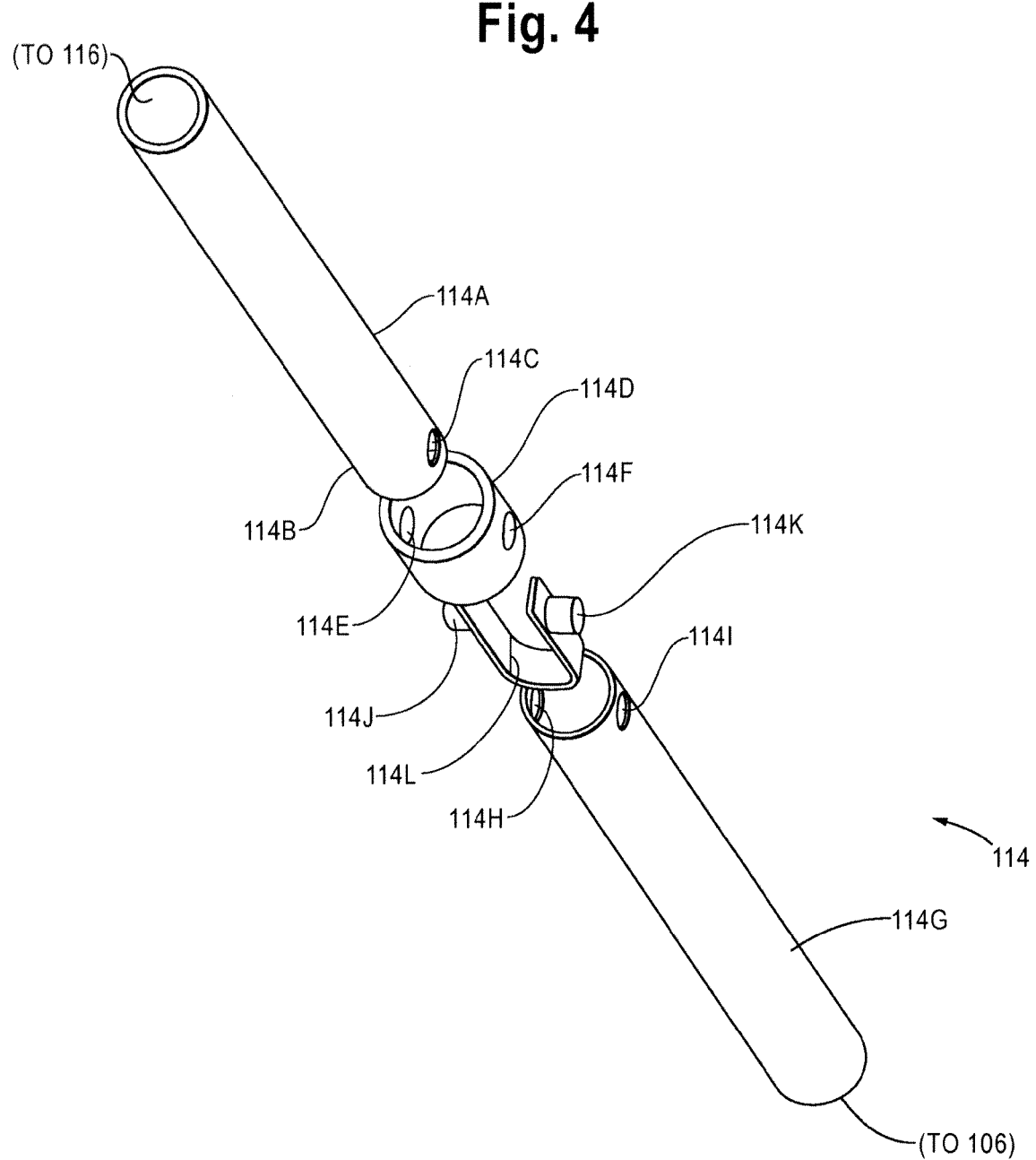
FIG. 4 is an exploded three-dimensional view of a telescopic pole assembly provided in accordance with various embodiments of the invention.

As illustrated in FIG. 4, various embodiments of the pole assembly 114 may include a lower pole section 114A connected in a telescoping configuration with an upper pole section 114B. As shown, a proximal end of the lower pole section 114A is connectable to the motor housing 106, and a distal end of the upper pole section 114B is connectable to the handle assembly 116. To facilitate the telescoping action of the pole assembly 114, the diameter of the lower pole section 114A may be configured to be greater than the diameter of the upper pole section 114B to facilitate receiving or sliding the upper pole section 114B into the lower pole section 114A, such as when the pole assembly 114 is in the contracted telescoping position. A connector collar 114C including portions 114D, 114E may be structured to at least partially engage a distal end of the upper pole section 114B and a distal end of the lower pole section 114A. The portions 114D, 114E may be connected to form the connection collar 114C by use of conventional fastening means such as screws 114F-114I, for example, which secure the connection collar 114C to the pole assembly 114, as shown.

In various embodiments of the pole assembly 114, a locking mechanism 114J may be positioned within a slot 114K of the connection collar 114C. The locking mechanism 114J may include a body segment 114L having a locking spring 114M connected at a first end of the body segment 114L. In operation, the locking spring 114M resiliently biases the first end of the body segment 114L outwardly from the connector collar 114C and promotes movement of a locking tab portion 114N of the body segment 114L inwardly toward the upper pole section 114C. In the extended telescoping position, the locking tab portion 114N may be received into a first slot 114O formed in the upper pole section 114C. In the contracted telescoping position, the locking tab portion 114N may be received into a second slot 114P formed in the upper pole section 114B. The locking tab portion 114N may be released from either of the slots 114O, 114P by depressing an area of the body segment 114L of the locking mechanism 114J adjacent to the locking spring 114M thus counteracting the resilient bias of the spring 114M. It can be seen that the resilient outward bias of the locking spring 114M serves to promote receipt of the locking tab portion 114N into the slots 114O, 114P, depending on whether an expanded or contracted telescoping position, respectively, is desired for use with the device 102.

One or more wheels 118, 120 may be operatively associated with the base 104A of the main housing assembly 104 to facilitate movement or travel of the device 102 across a cleaning medium. Also, a handle lock lever assembly 122 may be employed in the device 102 to permit locking or release of the angular movement of the collective arrangement of the handle assembly 116, the pole assembly 114, and the motor housing assembly 106 relative to the main housing assembly 104. It can be appreciated that permitting this relative angular movement enables convenient travel of the device 102 on the wheels 118, 120 across a cleaning medium such as by locomotion of a user, for example, employing the device 102.

In various embodiments, as shown in FIG. 1, a collection bin 124 may be removably received into a cavity within the main housing assembly 104 or elsewhere to receive organic or inorganic particles, substances, or infestation agents extracted from cleaning media through the base 104A of the main housing assembly 104 during vacuum operation of the device 102. A spring-released push button may be provided on the collection bin 124 to release a hinged bottom of the bin 124, thereby allowing collected materials to be released from the bin 124. The collection bin 124 may use a cone-shaped geometry to generate cyclonic action within the bin 124 that maximizes separation of collected material before air reaches a filter 125 at the back side of the collection bin. In certain embodiments, the collection function performed by the collection bin 124 can be instead achieved by a conventional bag-type arrangement, or another functionally equivalent device or mechanism that can be employed in the device 102 to collect debris, materials, and/or infestation agents extracted from various cleaning media by action of the device 102.

Movement of the organic or inorganic particles, substances, or infestation agents extracted from cleaning media to the collection bin 124 may be further facilitated by one or more airways, such as defined by passageway members 126, 128, as shown. The filter 125 may be positioned within a filter housing 130 and installed within the main housing assembly 104 to filter "dirty" air processed through the device 102 during a vacuum operation, for example. A replaceable, disposable filter 125 or a reusable filter may be used in conjunction with the collection bin 124 to capture debris or infestation agents extracted from cleaning media by operation of the device 102. In certain embodiments, HEPA filtration may be used to maximize the capture of various infestation agents extracted from cleaning media.

In various embodiments, a beater bar 132 may be positioned within the main housing assembly 104 and configured to rotate during a beater bar operational mode of the device 102. The beater bar 132 may be operatively associated with a beater bar motor 134, such as through a belt drive 136, to enable its rotation. The beater bar motor 134 may be a single-speed motor of AC or DC variety that powers the rotation of the beater bar 132 through a mechanical operative association with the belt drive 136. Alternately, a single motor can be employed to operate both the beater bar and vacuuming functions of the device. It can be appreciated that the beater bar 132 can be configured to rotate with sufficient speed to effectively impact the cleaning medium on which the device 102 is employed. For example, the beater bar 132 and beater bar motor 134 can be selected or configured so that carpet fibers can be effectively agitated on both higher and lower knap carpeting. In other examples, the beater bar 132 can be configured for effective sweeping of hard floor surfaces, mattresses, and/or furniture.

In various operational modes of the device 102, the rotating beater bar 132 may be structured to extract and carry infestation agents present within a cleaning medium to a surface of the medium and/or to within proximity of various portions of the base 104A of the main housing assembly 104 that are in the proximity of the cleaning medium. The beater bar 132 may include one or more beaters 132A, 132B, 132C extending therefrom that, during rotation of the beater bar 132, can function to act upon a cleaning medium, such as to agitate or spread fibers in a carpet or mattress, for example. The beaters 132 can be of solid construction, such as of rubber or plastic strips, or can be made of a plurality of bristles.

In various embodiments, a light bulb assembly 142 may be positioned within the main housing assembly 104. As described below in more detail, the light bulb assembly 142 may be structured to radiate UV light onto or into a variety of cleaning media upon which the device 102 may be employed. The UV light supplied by the light bulb assembly 142 may be configured to irradiate, sanitize, or otherwise disinfect a variety of infestation agents that may be present within a given cleaning medium. For example, the device 102 may use UV light radiated from the light bulb assembly 142 to sanitize dust mites living in the carpet flooring, mattresses, or furniture of a home or business.

In general, UV light wavelengths are considered less than about 400 nm and beyond the range of visible light. The UV portion of the light spectrum can be classified into three wavelength ranges: UVA (from 315 nm to 400 nm); UVB (from 280 nm to 315 nm); and, UVC (from 100 nm to 280 nm). In general, UV light with a wavelength shorter than about 300 nm is considered effective at killing micro-organisms including bacteria, viruses, and molds. In particular, research has shown that UVC light is optimal for killing micro-organisms. The UVC range of light wavelengths is commonly called the "germicidal" bandwidth, because light in this range can deactivate the DNA of microorganisms and destroy their ability to multiply. Specifically, UVC light causes damage to the nucleic acid of microorganisms by forming covalent bonds between certain adjacent bases in the DNA. The formation of such bonds prevents the DNA in the microorganism from being "unzipped" for replication, and the microorganism is unable to reproduce. When the microorganism tries to replicate, it is destroyed.

Research conducted in association with development of the invention has shown that dust mites often spend most of their time at or near the surface of cleaning media in which they are present, such as mattresses and carpeting, for example. It has also been discovered, however, that dust mite eggs and larvae may be at or near the surface, and/or deep within the cleaning media (e.g., buried in carpet fibers). The research has demonstrated that UVC light can be effective at disrupting the life cycle of microorganisms including dust mites, for example, if the UVC light is shined directly on the eggs and larvae of the microorganisms. As a result, various embodiments of the invention can be structured to achieve maximum irradiation within a cleaning medium (e.g., within carpet fibers). This irradiation can be achieved by placing the UV light source (e.g., light bulb) above or near protruding members that condition the cleaning medium to receive penetrating UVC light. It has been discovered that UVC light has the potential to break the life cycle of various microorganisms such as dust mites, for example, by killing the embryonic stage and thereby stopping the production of allergenic proteins in feces and exuviae. It was found that even a relatively small dose of UVC light had a fairly significant effect on dust mite reproduction, by affecting the rate of egg-laying and reproduction of the dust mites.

The effectiveness of UV light on infestation agents or microorganisms is directly related to the intensity of the light and exposure time. To be effective, the UVC light rays can be directed to strike a microorganism with sufficient intensity and exposure time to penetrate the microorganism and break down its DNA molecular bonds. It is important to understand that UV light acts on a cumulative basis. In other words, if the molecular bonds of a particular microorganism are not broken down on a first application of UV light emanating from the device 102, subsequent applications of UVC light will continue to break down the DNA on a cumulative basis with the prior applications. The dosage of UVC light (in terms of millijoules per square centimeter or "$mJ/cm^2$") is a product of light intensity (or irradiance) and exposure time. Intensity is measured in microwatts per square centimeter ($\mu W/cm^2$), and time is measured in seconds. In a given region irradiated with UVC light, for example, most microorganisms in the region can be eradicated with an efficiency of about four logs (that is, 99.99%) with a UVC dosage of about 40 $mJ/cm^2$. For example, if it is assumed that the UVC light intensity applied to a particular surface area of a cleaning medium is $2 \mu W/cm^2$, and the exposure time is 20 seconds, then the UVC light dosage would be 40 $mJ/cm^2$, thus eradicating or disinfecting about 99.99% of the microorganisms on the surface area. In numerous applications, UVC radiation of about 253.7 nm can be useful for eradication or disinfection of various kinds of microorganisms, although the invention is not limited to use at or near that range. In various embodiments, the disinfecting device may be configured to eradicate at least about 90%, or more preferably at least about 99% or 99.99%, of the infestation agents present within a cleaning medium during normal use.

Referring again to FIGS. 1 and 2, the light bulb assembly 142 may include a frame 142A having a generally curved reflector 142B attached thereto which is structured to receive and at least partially enclose or encase an ultraviolet light bulb 142C therein. The reflector 142B may be composed of a reflective material (e.g., highly polished aluminum) that can serve to re-direct or reflect UVC light emanating from the light bulb 142C toward the cleaning medium. The reflective surfaces may be smooth or faceted, specular or semi-specular, or diffusing and may be made of any reflective materials. The light bulb 142C may be, for example, a generally U-shaped, 35-watt, high-output, no-ozone bulb suitable for radiating light in the UVC wavelength range of light. Alternately, a single linear bulb or multiple linear or shaped bulbs can be employed. Further, a bulb-in-bar arrangement, as explained herein, can be used ion conjunction with other bulbs. The bulb 142C may be powered by insertion into a socket 142D which may be electrically connected to a ballast 144 or another power source. In certain embodiments, the ballast 144 may be a 120 VAC, 800 mA ballast, for example.

It can be appreciated that the intensity of radiation emitted from a UV light source (e.g., the light bulb 142C), and the associated disinfecting effectiveness of the radiation, are a function of the proximity of the UV light source to the cleaning medium. The inventors have discovered that, for certain applications and embodiments of the devices described herein, the light bulb 142C may be positioned no more than about 2 inches from a surface of the cleaning medium, more preferably no more than about 1 inch from the surface of the cleaning medium, and most preferably no more than about 0.5 inches from the surface of the cleaning medium, to maximize the effectiveness of the devices in disinfecting infestation agents present within a cleaning medium.

Figure 2:
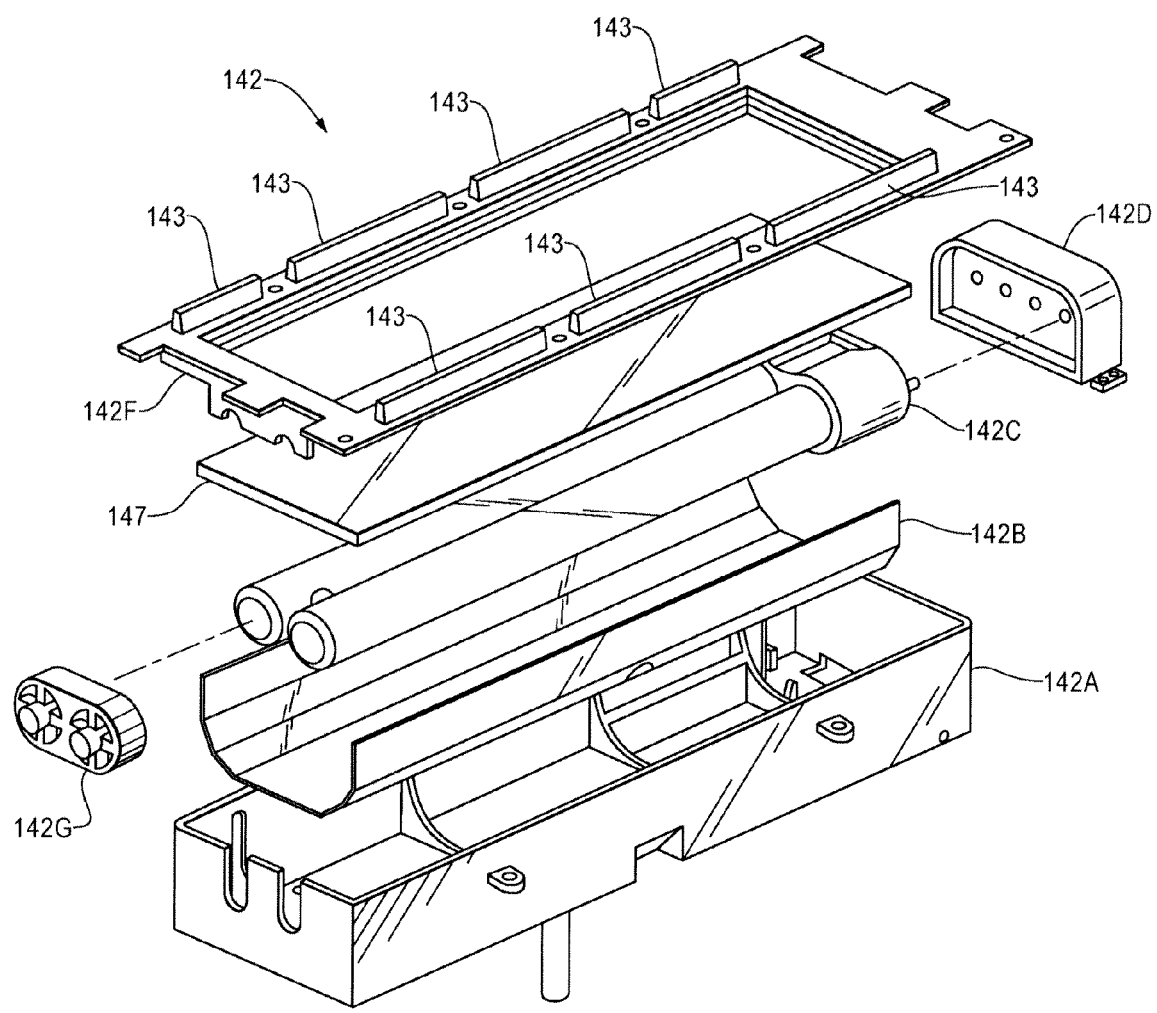
FIG. 2 is an exploded three-dimensional bottom-to-top view of the light bulb assembly of the device shown in FIG. 1.

It can further be appreciated that the dosage of the UV radiation is a function of the time of exposure of the cleaning medium to the radiation. To this end, it is a purpose of the invention to provide embodiments which provide for sufficient duration of exposure of the infestation agents to the UV radiation. As seen in FIG. 2, multiple UV bulbs can be employed, which when the device is in use, will approximately double the amount of time the UV light irradiates any given area of cleaning medium over a single linear bulb design at a given rate of speed. Alternately, a U-shaped bulb can be employed, which will approximately double the exposure time over a single linear bulb at a given rate of travel. The device can employ multiple linear and/or shaped bulbs. Alternate arrangements can be employed as well, such as at least one bulb in front of and at least one bulb behind the beater bar, as seen in FIG. 5A.

The arrangement, shape and number of bulbs will effect the duration of exposure of the cleaning medium at a given rate of travel of the device. Obviously reaching a target dosage of 30-40 $mJ/cm^2$ is more easily achieved under normal use conditions if that dosage can be reached in 1-3 seconds of exposure. That is, a normal user is less likely to use the device slowly enough to expose the cleaning medium for a lengthy period of time, such as 20 seconds. The device is preferably designed such that at a normal rate of use, that is, at a normal or slow walking pace, any given area of cleaning medium will be exposed for a duration of time sufficient to eradicate 90% of infestation agents, or more preferably 99% or 99.99% of eradication. The arrangement of the bulb or bulbs can be designed to expose an area of cleaning medium, at a slow to normal walking pace, to at least one second of exposure to UV light and more preferably for about two seconds or more of exposure. The desired duration of exposure will vary depending on the intensity of the radiation as determined by the distance from the light source to the cleaning medium, the power of the light source and the effectiveness of reflectors.

A lens 147 may be included in the light bulb assembly 142 positioned in a lens frame 142F, and this arrangement may serve to protect the light bulb 142C from breakage and/or direct contact with surfaces or other objects. To further protect the light bulb 142C from shock and vibration effects, an isolator 142G or shock absorber or dampener can be employed. The shock dampener can be made of rubber or another suitable material and be positioned on one or more if the distal ends of the light bulb 142C, as shown in FIG. 2. In certain embodiments, foam or rubber cushions and/or suspension supports may be positioned adjacent to the light bulb 142C and/or around the socket 142D to absorb forces or vibration arising from operation and use of the device 102.

The lens 147 is preferably disposed between the light source or bulb 142C and the cleaning medium. The lens resists direct human contact with the light bulb 142C, which is advantageous because the presence of finger prints, for example, on the light bulb 142C may hinder transmittance of UVC light during operation of the device 102. In the event the light bulb 142C breaks, for example, it can be seen that the lens 147 promotes containment of light bulb 142C fragments within the assembly 142. The lens 147 is made of a substantially translucent material. In certain embodiments, the lens 147 may be composed of a relatively thin (e.g., about 3 mm) fused silica or quartz glass, or a substance that allows greater than 80% transmittance of UV light therethrough. More preferably, the lens 147 allows greater than 90% transmittance of UV light, or 95% transmittance or higher. The thickness of the lens can vary, although typically the thinner the lens the better the transmittance. Accordingly, a thinner lens is preferable, in one embodiment a lens of no more then three mm is preferred.

Adjacent to the lens 147, or directly below the lens 147, at least one protruding member 143 extends from the device and into contact with the cleaning medium. Preferably the protruding members 143 extend from the lens frame 142F or from the lens 143 itself. During operation of the device 102, the protruding members 143 serve to act upon the cleaning medium (e.g., by contacting the medium and spreading open a section of carpet flooring or a mattress) to promote penetration of UV light into the cleaning medium. The protruding members 143 may also serve to prevent leakage reflection of UV light rays away from the interior of the light bulb assembly 142. Although a single protruding member can be employed, a plurality is preferred.

Figure 2A:
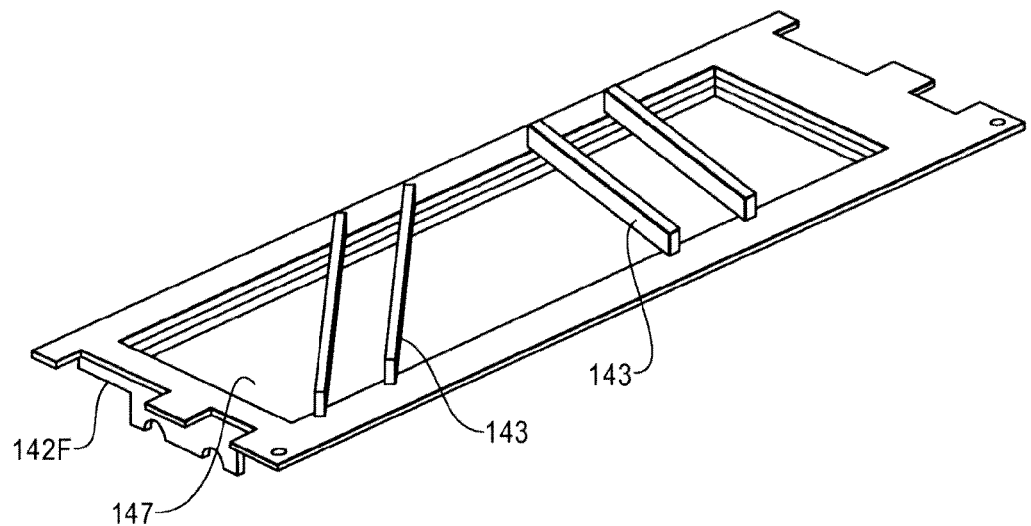
FIG. 2A is a perspective view of one embodiment of a lens frame of the device.
Figure 2B:
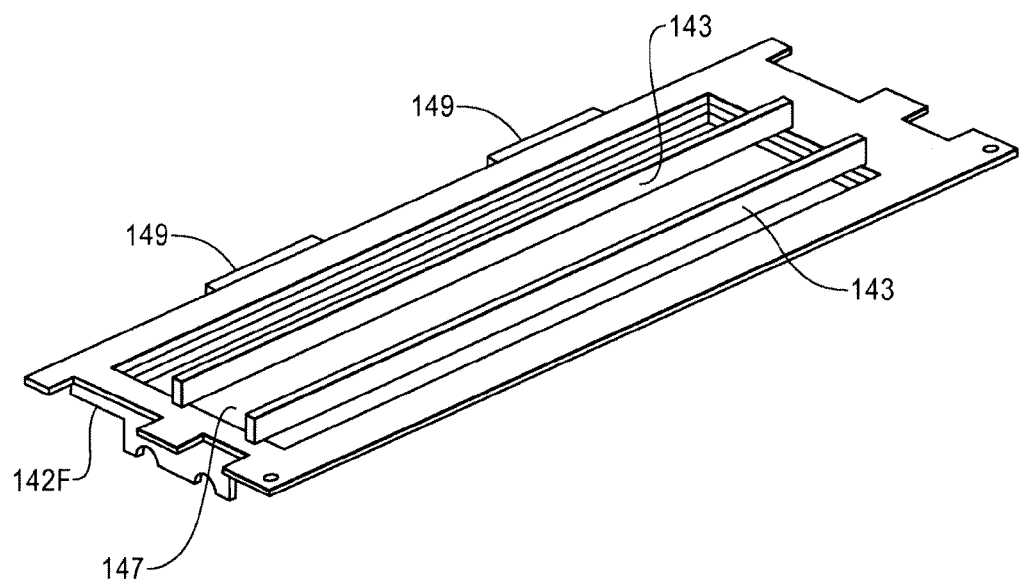
FIG. 2B is a perspective view of one embodiment of a lens frame of the device.
Figure 3:
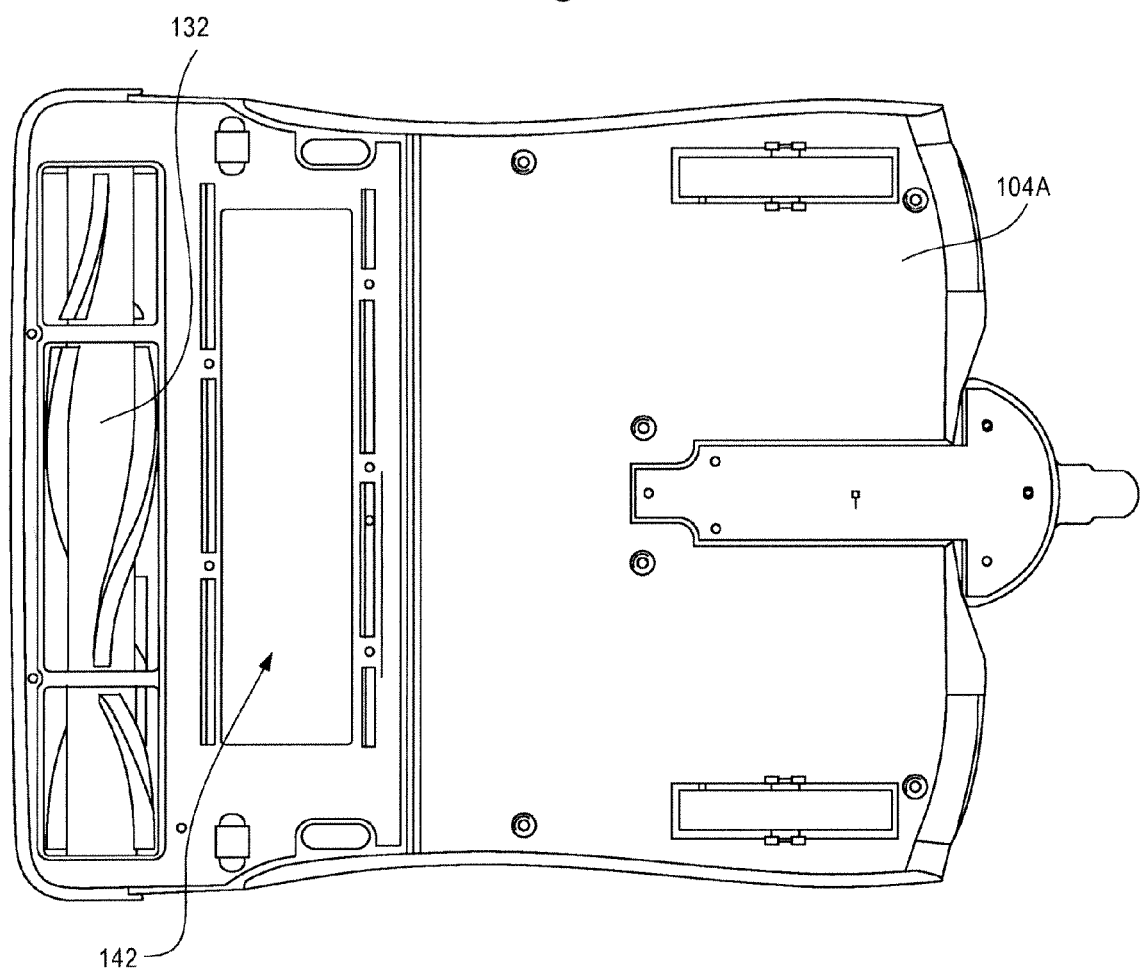
FIG. 3 is a plan view of a portion of the main housing assembly of the device of FIG. 1.
Figure 5:
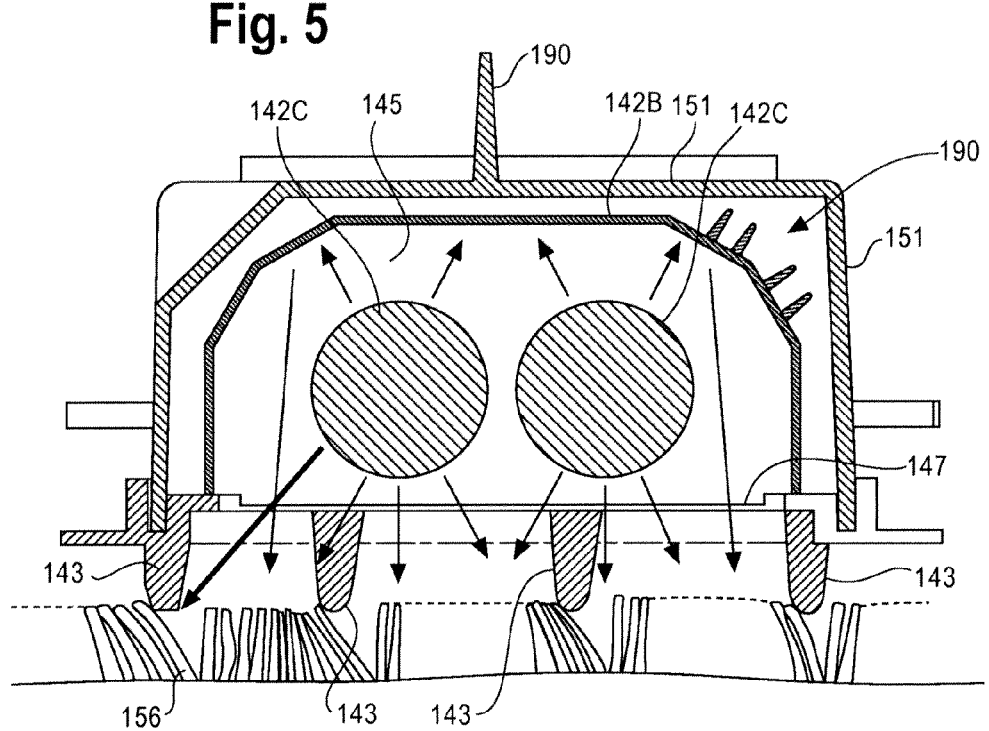
FIG. 5 is a schematic cross-sectional view of a portion of a disinfecting device provided in accordance with various embodiments of the invention.
Figure 5A:
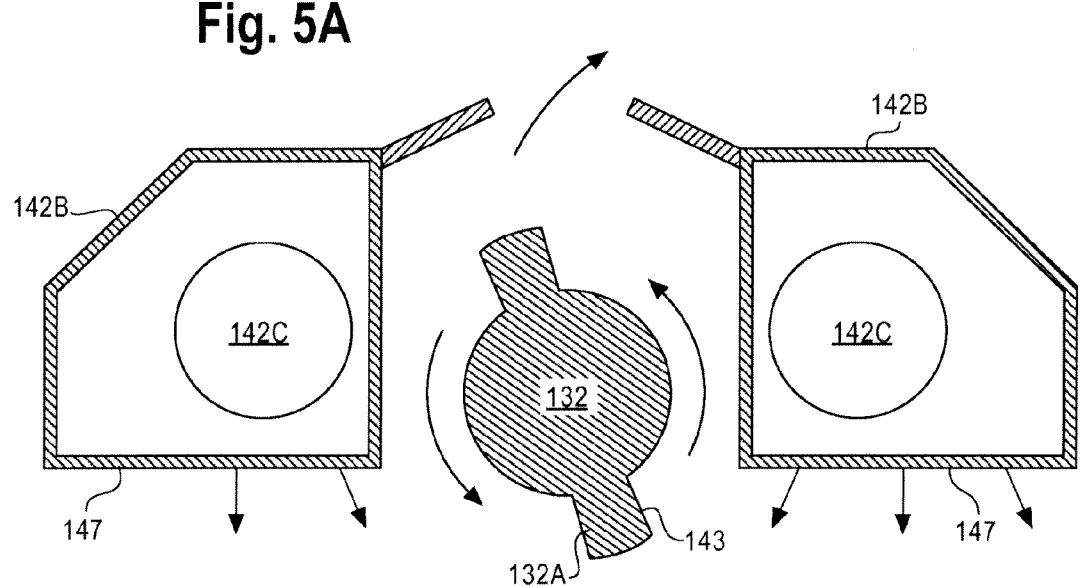
FIG. 5A is a schematic cross-sectional view of a portion of a disinfecting device provided in accordance with various embodiments of the invention.

The protruding members 143 can be arranged variously, such as seen in FIGS. 2, 2A-B and 5. In FIG. 2, the protruding members are arranged adjacent the lens 147, both in front of and behind the lens and UV light source 142C. Alternately, as seen in FIGS. 2A and 2B, the protruding members can extend across the lens and across the UV light source 142C. The protruding members 143 can extend across the lens 147 longitudinally, as in FIG. 2B, or diagonally or laterally, as seen in FIG. 2A. Preferably, the protruding members are attached to the lens frame 142F, as seen in FIGS. 2, 2A-B and 3. Alternately, as seen in FIG. 5, the protruding members can extend directly from the lens itself. For example, the lens 147 can be manufactured to include protruding members 143 therefrom or such members may be attached to the lens by adhesives and the like. The protruding members 143 can be opaque, translucent or transparent and can be made of rubber, plastic or other materials. Alternately the members 143 can be made of a plurality of bristles. The members 143 can be flexible or inflexible, but should be stiff enough to effectively move carpet fibers. If the protruding members extend across the direct path of the UV light, it may be preferable that they transmit UV light through to the cleaning medium.

As seen in FIG. 5, the protruding members 143 at least partially fall in the direct path of UV light irradiated form the UV light source 142C, as seen by the path of rays (as indicated by arrows). The protruding members 143 are designed to contact a carpet cleaning medium, pushing the fibers of the carpet apart to create space for the direct shining of UV light upon areas of the fibers that would not otherwise receive direct radiation. As the device 102 is moved back and forth over the carpet cleaning medium, the protruding members 143 act to open up the medium to direct UV light. In this manner, the deeper areas of the medium which may bear infestation agents, especially eggs, are subject to irradiation. In FIG. 5, the device 102 is seen moving right to left, opening up the carpet fibers as the protruding members contact and force apart the fibers. As the device is moved in the opposite direction, the protruding members will again create space between the fibers allowing UV light to reach into previously hidden portions of the cleaning medium. Since the effect of UV radiation on infestation agents is cumulative, the protruding members are designed to allow a greater combined duration of exposure as the device is moved back and forth across the cleaning medium.

The protruding members 143 may be stationary, as seen in FIGS. 2, 2A-B and 5, or can be designed to move relative to the device 102. For example, in an embodiment employing the bulb-in-bar assembly, as explained herein, the beaters of the beater bar serve as protruding members 143 since they fall in the path of the light source 142C. In such a case, the protruding members are not stationary, but move independently with respect to the light source.

The lens frame 142F can be removably or pivotally attached to the device housing, such as by latches 149 or other known mechanisms so that the lens frame can be moved away from the lens to facilitate cleaning of the lens.

In another embodiment of the device, the lens 147 is not supported above the surface of the cleaning medium. Rather, the lens is designed to contact the medium as the device is moved across the medium surface. In such a way, the lens is constantly wiped during use, thereby removing any dust that may otherwise adhere to the exterior of the lens 147. Since UV light is absorbed so readily, dust build-up on the exterior of the lens will adversely effect the disinfecting capabilities of the device. Consequently, the lens may be cleaned between uses by the user or, in the embodiment just described, use of the device will also constitute a method for removing dust from the lens.

As shown schematically in FIG. 5, the light bulb 142C may be positioned in an inner bulb chamber 145 of the light bulb assembly 142. The bulb chamber 145 can be formed of various components but must provide for positioning of the bulb or bulbs 142C therein. Radiant energy or light beams (depicted schematically by the representative arrows illustrated in FIG. 5) emitted from the light bulb 142C shine directly or indirectly from the light bulb 142C onto and/or into a cleaning medium 146. It can be seen that light beams incident on the reflector 142B can be reflected back from the reflector 142B toward the cleaning medium 146 to further enhance the effectiveness of the light bulb assembly 142 in disinfecting or sanitizing infestation agents residing within the cleaning medium 146.

Figure 7:
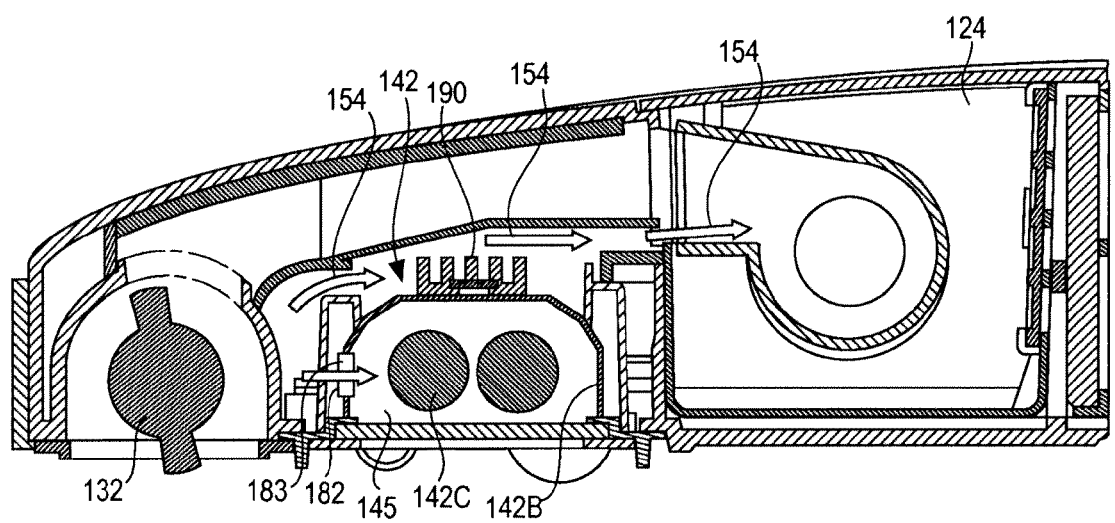
FIG. 7 is a schematic cross-sectional view of a portion of a disinfecting device provided in accordance with various embodiments of the invention.

The inner bulb chamber 145 may be formed by the collective arrangement of chamber walls 151 and the lens 147 to create an ambient environment around the light bulb 142C, as seen in FIG. 5. Alternatively, the chamber walls 151 can be comprised of or incorporate a portion or the entirety of the reflector 142B. Such an arrangement is seen in FIG. 7. Preferably, the bulb chamber is substantially dust-tight. That is, the bulb chamber remains substantially free of dust and other particles during use. To this end, various seals and gaskets can be employed to better seal the chamber. Since about 90% of all particles are smaller than 0.3 microns, the chamber is preferably designed to substantially prevent infiltration by particles of that size or even smaller. It is important to prevent dust in the chamber since such dust will tend to collect on the exterior of the UV light bulb 142C and act to absorb the emitted UV light, preventing the UV light from reaching the cleaning medium. The chamber can further be airtight. The chamber, in the embodiment of FIG. 5, is defined primarily by the chamber walls 151 and lens 147. Consequently, the walls and lens preferably are sealed against substantial dust intrusion. In this embodiment, the reflector 142B need not create a separate sealed chamber, although it is depicted as doing so, as it is entirely enclosed within the bulb chamber created by the walls 151 and lens 147. In another embodiment, as seen in FIG. 7, wherein the reflector 142B comprises a bulb chamber wall, the reflector and lens preferably create a chamber substantially or wholly sealed against dust particles.

In one example of an experiment conducted in association with development of the invention, conditions used in developing the light bulb 142C specifications were as follows: a desired dosage of 40 mJ/cm² was selected in order to achieve about 99.99% eradication of most microorganisms; the device 102 was moved at a relatively slow walking pace across a carpet cleaning medium, exposing any particular area of the carpet to approximately two seconds of UVC light; the light bulb 142C was positioned about 0.5 inches from the surface of the carpet; the beater bar 132 was employed to optimize bringing microorganisms to the surface of the carpet for maximum exposure to the UVC light; and, the reflector 142B was employed. With these experimental conditions, it was determined that a generally U-shaped, 42-watt, 8.7 inch light bulb 142C generated approximately 12.6 µW/cm² of UVC irradiance. With the addition of the polished, curved aluminum reflector 142B behind the light bulb 142C in the light bulb assembly 142, the UVC irradiance generated was in the range of approximately 20 µW/cm². With one second of exposure, it was discovered that this configuration for the light bulb assembly 142 generated approximately 20 mJ/cm² of a UVC light dosage; with two seconds of exposure, the configuration generated approximately 40 mJ/cm² of UVC light dosage to achieve the desired four logs (i.e., 99.99%) eradication of microorganisms. A specific example involving the influenza virus helps to illustrate the dosage needed: to eradicate influenza virus in the carpeting with the above experimental conditions, a UVC light dosage of 6.6 µW/cm² would be needed. This UVC light dosage could be achieved in the first 0.33 seconds of passing the UVC light bulb 142C over the influenza virus in the carpet. The exposure time of any given area of cleaning medium will, of course, be greater than that achieved on a single pass of the device since most users will not simply walk across the area but will rather push and pull the device over the same area multiple times.

Figure 6:
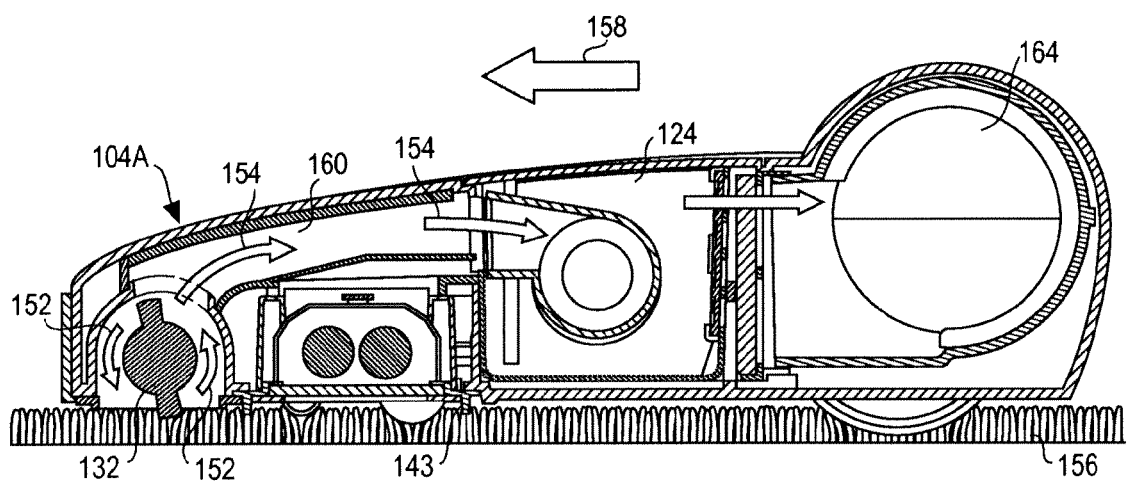
FIG. 6 is a schematic cross-sectional view of a portion of a disinfecting device provided in accordance with various embodiments of the invention.

In various embodiments of the invention, it may be desirable to employ structures or mechanisms that facilitate heat dissipation within or in the immediate vicinity of the light bulb assembly 142, such as to control the ambient air temperature in the bulb chamber 145. With reference to FIG. 6, solid arrows 152 represent rotation of the beater bar 132 as it acts upon a cleaning medium 156 during travel of the device 102 (represented schematically by arrow 158) during operation. In association with operation of the device 102, as shown schematically by representative arrows 154, air flow can be facilitated by negative pressure generated by action of the vacuum motor 110. The air flows from the beater bar 132 through a collection bin airway 160, through the collection bin 124, and then through a vacuum motor airway 162 leading to the vacuum motor 110.

In various embodiments, heat transfer may be effected by structuring the chamber walls 151 for exposure to cooling air flow through the device 102, such as air flow generated during a vacuum operation. It can be appreciated that operation of the light bulb 142C within the inner bulb chamber 145 of the light bulb assembly 142 can generate heat in the ambient environment or air around the light bulb 142C. The temperature of the ambient environment within the bulb chamber 145 can impact performance or effectiveness of the light bulb 142C. Thus, in certain embodiments, it is desirable to structure the chamber walls 151 from conductive material or materials that conduct heat from the inner bulb chamber 145 and into contact with the airflow streaming through the device 102, such as during a vacuum operation. Examples of suitable materials that may be used for the chamber walls include aluminum, aluminum alloys, or other metals that can adequately conduct heat away from the inner bulb chamber 145. In certain embodiments, where the chamber walls 151 are coextensive with the reflector 142B, the reflector 142B is comprised of material that is both a reflective and heat conductive material.

In certain embodiments, and with particular reference to FIG. 7, one or more airflow holes, such as airflow hole 182, may be formed in the chamber walls 151 adjacent to an airflow stream. The pressure differential between the ambient air inside the inner bulb chamber 145 of the light bulb assembly 142 and the airflow stream 154 external to the inner bulb chamber 145 may be configured to draw air, and heat recumbent in the air, from the inner bulb chamber 145 into the airflow stream 154. In various embodiments, one or more airflow inlet holes may be formed generally adjacent to the isolator 142G, or one or more airflow outlet holes may be formed in the chamber walls 151 or reflector 142B adjacent to the airflow stream.

In various embodiments, as shown in FIGS. 5 and 7, a fin assembly 190 including one or more fins may be connected to the reflector 142B to further increase the capability to transfer heat from the inner bulb chamber 145 to the airflow stream. As seen in FIG. 7, the fin assembly 190 is mounted or formed directly on the reflector 142B, since the reflector forms a chamber wall. Alternatively, where the chamber wall 151 does not include the reflector 142B, as seen in FIG. 5, the fin assembly 190 is preferably formed or mounted on the chamber wall 151. Also seen in FIG. 5 are fin assemblies 190 on the reflector 142B.

In an arrangement which includes airflow holes in the chamber 145, it is preferable to use an air filter 183 to filter the airflow entering the chamber. The air filter 183 preferably eliminates dust and other airborne particles from reaching the interior of the chamber. As explained above, the chamber is preferably dust tight. Consequently, the air filter 183 is preferably effective to eliminate most particles of 0.3 microns or even smaller.

It can be appreciated that such air flow engineering can be beneficial for thermodynamically transferring heat away from the inner bulb chamber 145 to enhance the effectiveness of the radiant energy supplied by the light bulb 142C. In certain embodiments of the light bulb 142C, for example, it has been discovered that the effectiveness of UVC light radiance is reduced when the ambient air temperature around the bulb 142C rises above about 110 degrees Fahrenheit and higher. The device is preferably designed, therefore, with a heat dissipation system effective to maintain the bulb chamber at 110 degrees Fahrenheit or lower. Further, the device can employ a temperature sensor and associated indicator light or switch-off to alert the user to the elevated temperature or switch off the device to allow cooling.

Figure 8:
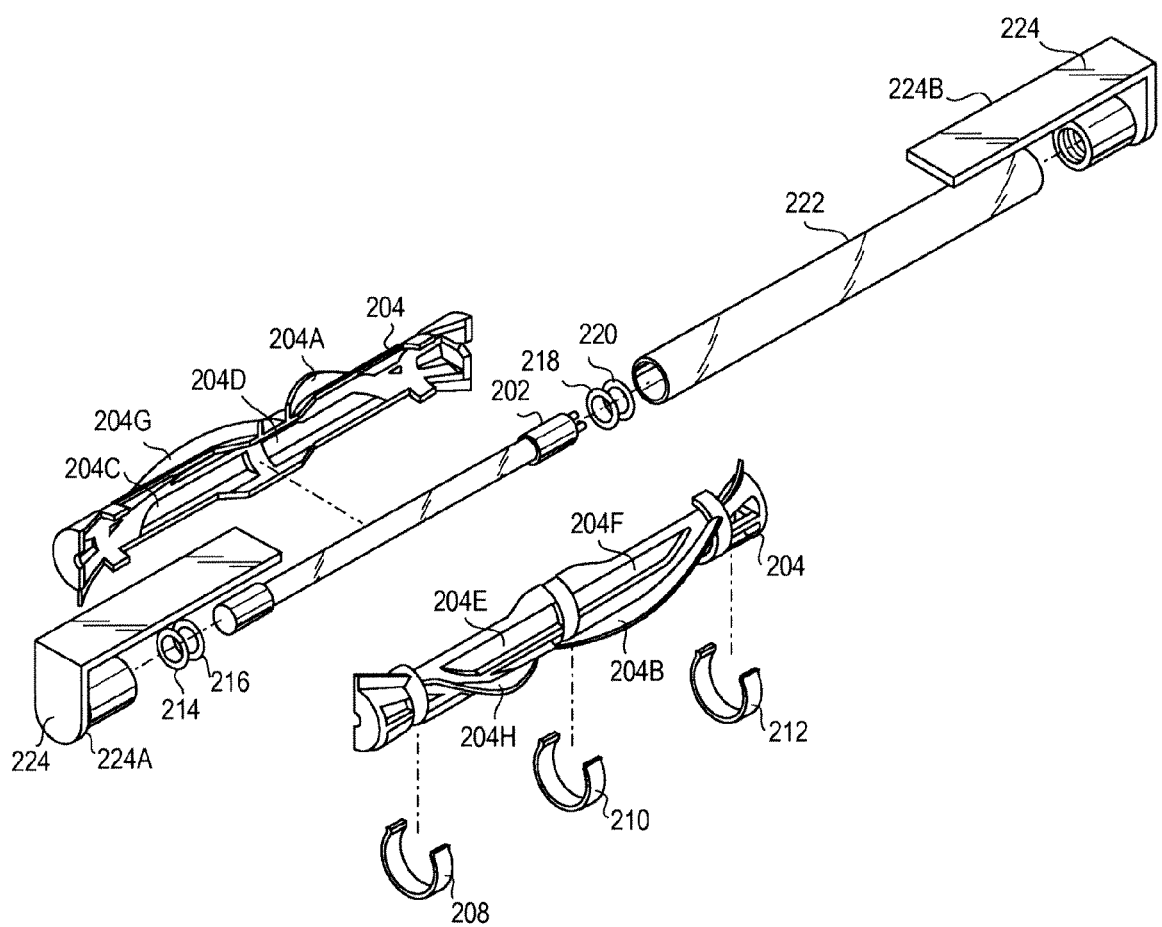
FIG. 8 is an exploded three-dimensional view of a bulb-in-bar assembly provided in accordance with various embodiments of the invention.

With reference to FIG. 8, in various embodiments, the light bulb 202 and the beater bar 204 may be integrated into a single bulb-in-bar assembly 206 for use in a disinfecting device. As shown, the light bulb 202 may be at least partially encased by a skeleton frame 204 including first and second skeleton portions 204A, 204B which collectively form the beater bar 204. Openings 204C-204F may be formed in the beater bar portions 204A, 204B permit UV light radiated from the light bulb 202 to escape from the bulb-in-bar assembly 206. It can be appreciated that, in certain embodiments, the skeleton portions 204A, 204B of the skeleton frame beater bar 154 may be replaced by a single-piece skeleton frame structured to at least partially encase the light bulb 202 therein. As shown, one or more beaters 204G, 204H formed on the beater bar portions 204A, 204B function to condition or beat a cleaning medium, such as the fibers of a carpet floor, to bring infestation agents towards or to the surface of the cleaning medium. In the bulb-in-bar embodiment, the beaters also can function as protruding members, as explained above, extending into the cleaning medium and separating carpet fibers for direct exposure to UV light emanating from the UV bulb. The beater bar portions 204A, 204B may be secured by the use of one or more C-clamps 208, 210, 212 to hold the beater bar 204 together and to maintain the light bulb 202 securely within the bulb-in-bar assembly 206. In addition, one or more rubber O-rings 214, 216, 218, 220 may be employed to protect the light bulb 202 from shock and vibration. In certain embodiments, a protective sleeve or lens 222 comprised of a transparent material, such as quartz glass or fused silicon, may be positioned underneath the beater bar portions 204A, 204B, and outside of the light bulb 202 to at least partially encase and protect the light bulb 202 from contact with objects, materials, or infestation agents. The bulb-in-bar assembly 206 may be positioned within a frame 224, including first and second frame portions 224A, 224B as shown, which facilitates rotation of the bulb-in-bar assembly 206 during operation of the device 102. It can be appreciated that the bulb-in-bar assembly 206 can serve to maximize penetration of UV light irradiation into a cleaning medium.

As with other embodiments of the device, it is preferable that the bulb chamber in the bulb-in-bar assembly be substantially or wholly dust tight as described above. Consequently, the bulb-in-bar assembly will employ gaskets and seals as needed or desired.

Figure 9:
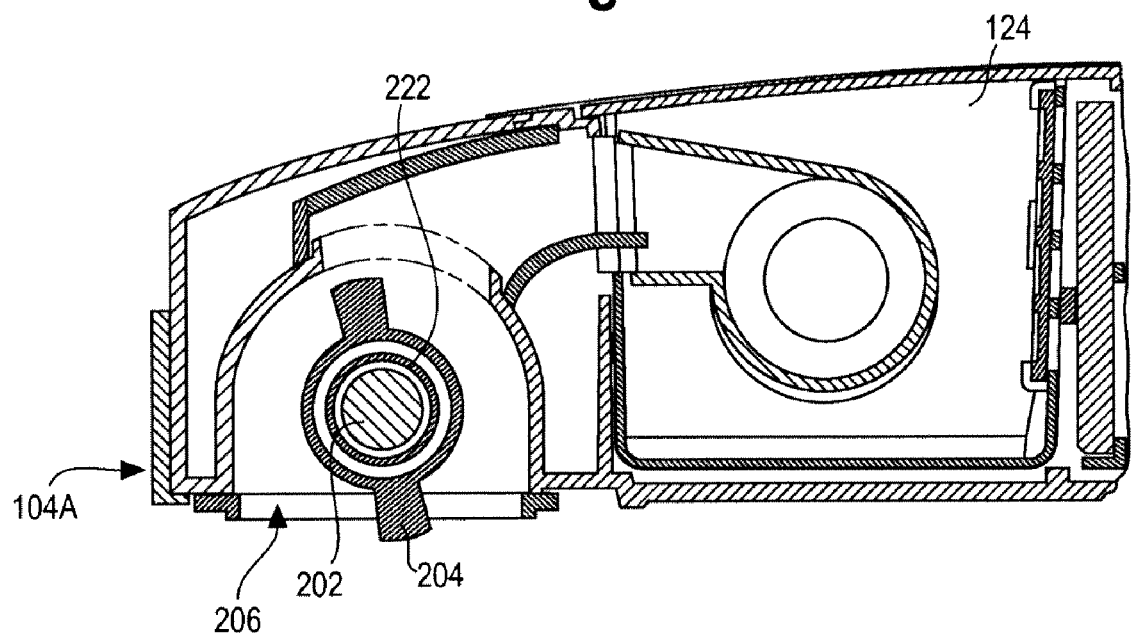
FIG. 9 is a cross-sectional view of a portion of a disinfecting device provided in accordance with various embodiments of the invention.

The schematic of FIG. 9 illustrates that, for certain embodiments of a modified device 102, the bulb-in-bar assembly 206 may be installed for operation. In view of the light bulb 202 being included within the beater bar skeleton frame 204, it can be seen that a separate light bulb assembly 142, as described above, is not required. The bulb-in-bar assembly can be used in conjunction with other UV bulbs, however. Otherwise, the various features of the device 102 can be readily structured for applicability to the embodiment of the device as illustrated in FIG. 9.

Figure 10:
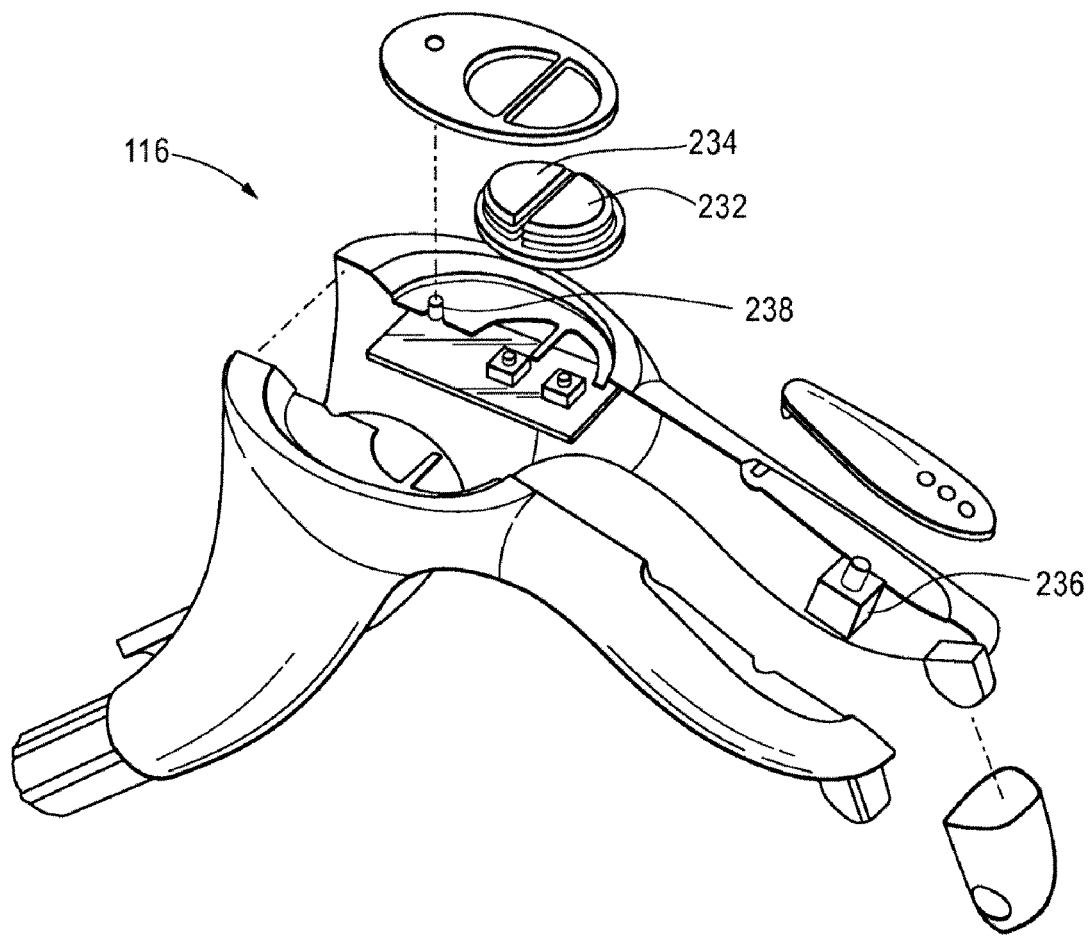
FIG. 10 is an exploded three-dimensional view of the handle of the device shown in FIG. 1.

With reference to FIG. 10, a main power switch 232 and a beater bar on/off switch 234 may be located on the handle assembly 116 of the device 102 or elsewhere on the device 102, such as on the main housing assembly 104, for example. The main power switch 232 enables the device 102 to receive power from an external power source or battery. The beater bar on/off switch 234 enables rotation of the beater bar 132 in various operational modes of the device 102. In addition, a safety switch 236 may be positioned on the top, bottom, or other user-accessible portion of the handle assembly 116 that can be configured such that the safety switch 236 must be depressed or activated during operation of the device 102 to permit the light bulb 142C to be activated. Likewise, when not depressed or activated, the safety switch 236 can be configured to either deactivate the light bulb 142C, or otherwise not permit the light bulb 142C to be activated until the safety switch 236 is depressed. One or more indicators 238 may be provided on the handle assembly 116 and/or the main housing assembly 104, for example, to communicate activation of the light bulb 142C to a user of the device 102. For example, the indicator 238 may be configured to be lit when UVC light is being radiated from the light bulb 142C to indicate to a user that disinfection of the cleaning medium is underway. It can be appreciated that positioning the safety switch 236 on the handle assembly 116 in certain embodiments promotes keeping the user at a minimum distance from the radiance of the light bulb 142C when the light bulb 142C is activated during operation of the device 102.

The safety switch 236 is preferably a dead man's switch or deadman device. That is, the switch is designed to shut of or deactivate the UV light source in case the user becomes incapacitated or otherwise ceases activation of the deadman switch. This fail safe mechanism is designed to prevent the user from direct exposure to the UV light. The safety switch can be of any type known in the industry, can employ a trip cord, be a simple trigger or depression switch, or be of other design.

Figure 11:
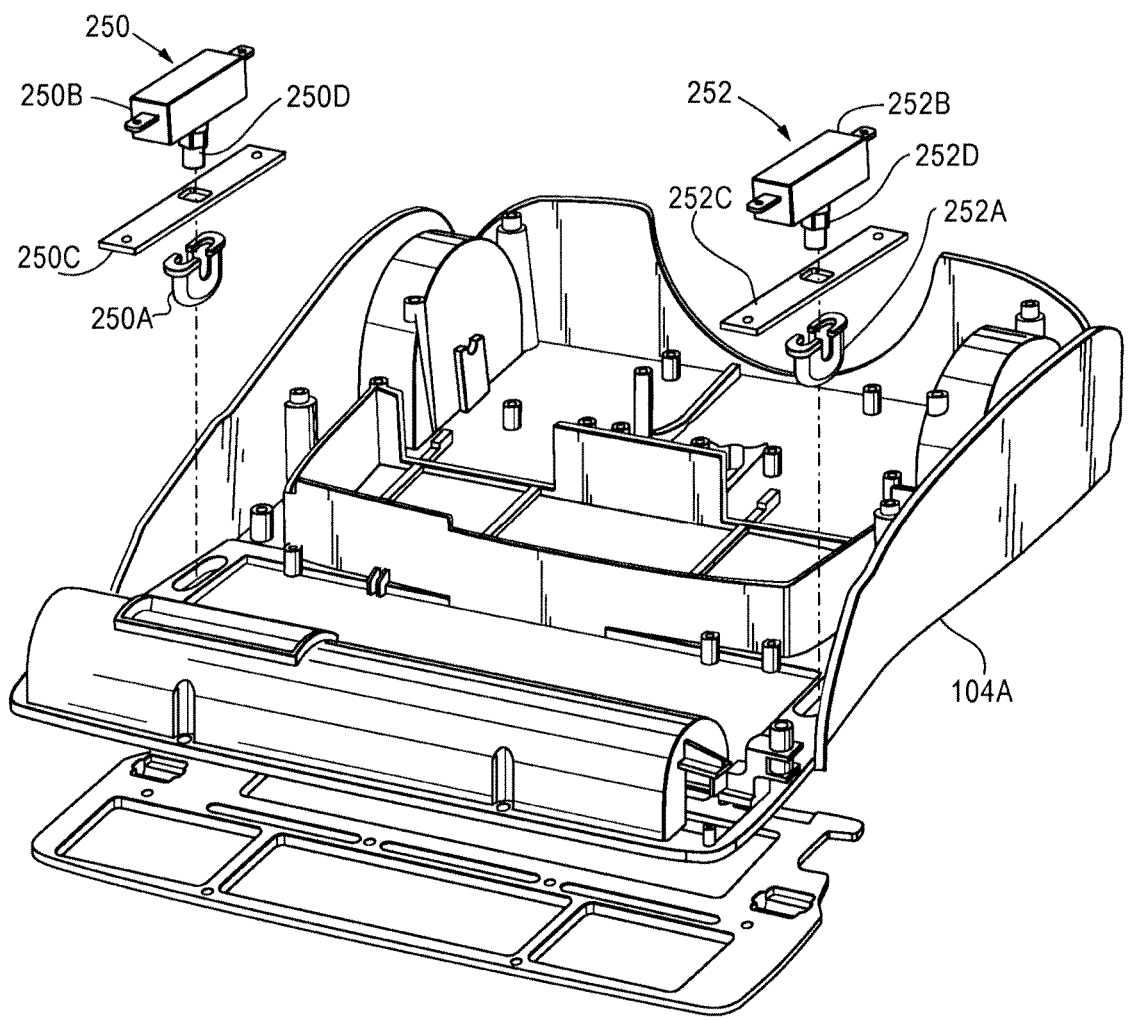
FIG. 11 shows an exploded three-dimensional view of the device of FIG. 1 in association with various cleaning medium contact switch assembly embodiments of the invention.
Figure 12:
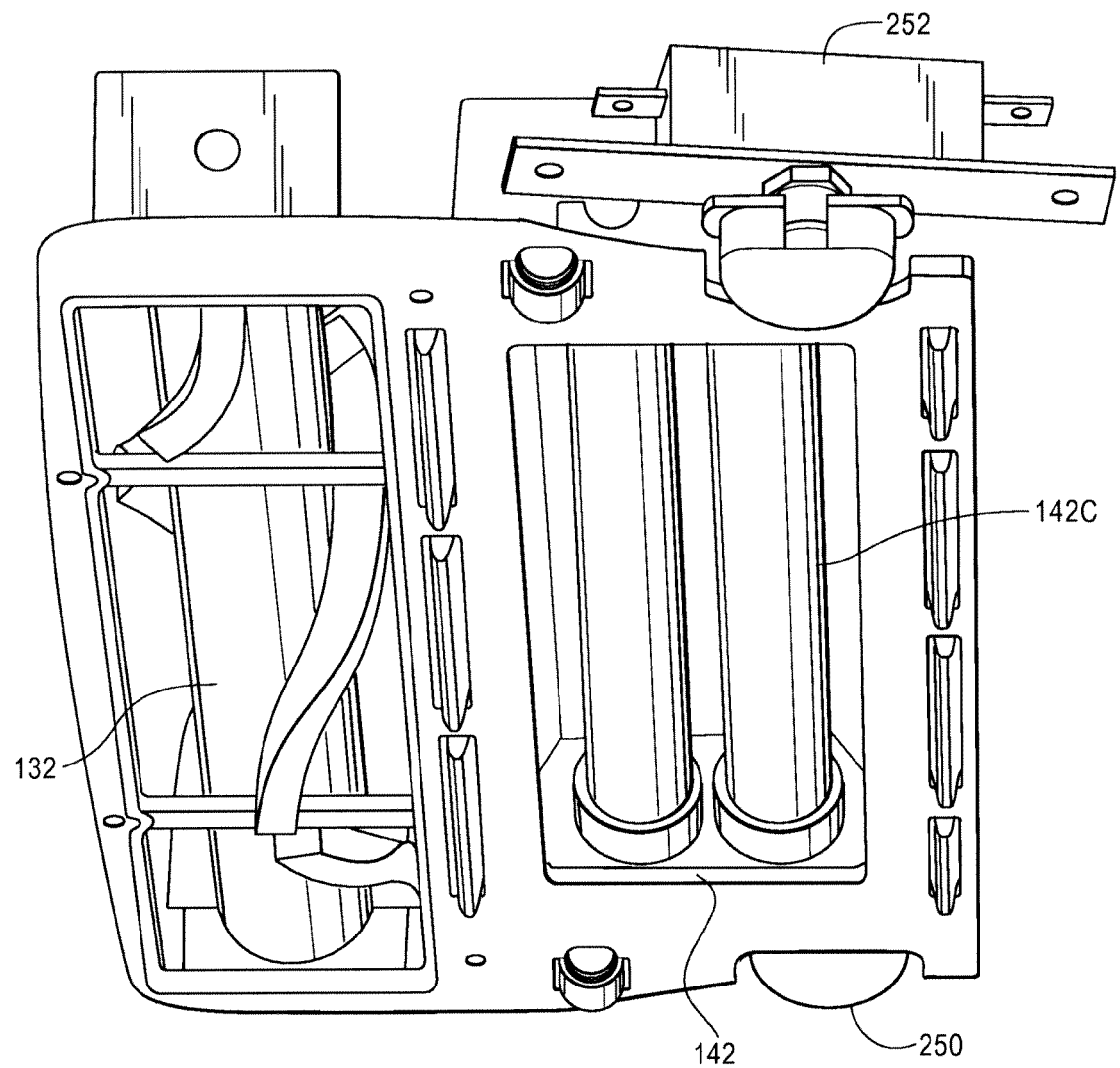
FIG. 12 illustrates a partially cut-away, three-dimensional view illustrating aspects of the cleaning medium contact switch assembly embodiments of FIG. 11.

With reference to FIGS. 11 and 12, one or more cleaning medium contact switch assemblies 250, 252 may be positioned in operative association with the base 104A of the main housing assembly 104. Each of the cleaning medium contact switch assemblies 250, 252 includes a floor or cleaning medium contact portion 250A, 252A (respectively), connected to an electrical switch portion 250B, 252B (respectively), through a mounting plate 250C, 252C (respectively), as shown. During operation of the device 102, the weight of the device 102 is sufficient to activate the push button switches 250D, 252D and allow activation of the UV light source. Preferably, the switch assemblies also function to communicate an electrical signal that lights bulb 142C to alert the user that the switches are depressed and the UV light is active. In various embodiments, each contact portion 250A, 252A may be covered by a generally rounded, durable plastic material structured to minimize friction with a cleaning medium when the device 102 travels across the cleaning medium. In certain embodiments, it can be appreciated that the cleaning medium contact switch assemblies 250, 252 prevent activation of or deactivate the light bulb 142C when the device 102 is lifted or tilted away from the cleaning medium, thus releasing one or both of the push button switches 250D, 252D. This prevention of activation or deactivation of the light bulb 142C may be configured to occur even if the safety switch 236 is already activated in a mode (e.g., in a depressed state) that would normally permit or enable activation of the light bulb 142C.

Other safety switches may be employed as are known in the art. Such switches include various dead-man switches, whether located on the handle assembly or elsewhere. Other contact switches or proximity switches may be employed, such as an optical or laser switch operable to cut off power to the UV bulb if a cleaning surface is not within a prescribed distance. A motion sensor and safety switch which operates to shut off the UV bulb when the device is stationary can be used, whether the switch is keyed to motion of the device, turning of the device wheels or otherwise. Similarly, other motion sensors and switches or gravity switches may be employed.

In various embodiments, it can be appreciated that multiple safety mechanism can be employed. For example, the cleaning medium contact switch assemblies 250, 252 may be configured to cooperate in conjunction with the deadman safety switch 236, and/or in association with other safety features such as the airflow engineering embodiments described above, to provide a multiple and integrated safety system for the device 102. For example, the cleaning medium contact switch assemblies 250, 252 and the safety switch 236 may be electrically connected in series such that if one or both switches are opened the light bulb 142C is electrically disconnected from its power source and deactivated. The cleaning medium contact switch assemblies 250, 252 and the safety switch 236 may be further electrically configured upon deactivation to only turn off the light bulb 142C, and not otherwise disable other operational modes of the device 102 (e.g., vacuum cleaning action or rotation of the beater bar 132).

Figure 13:
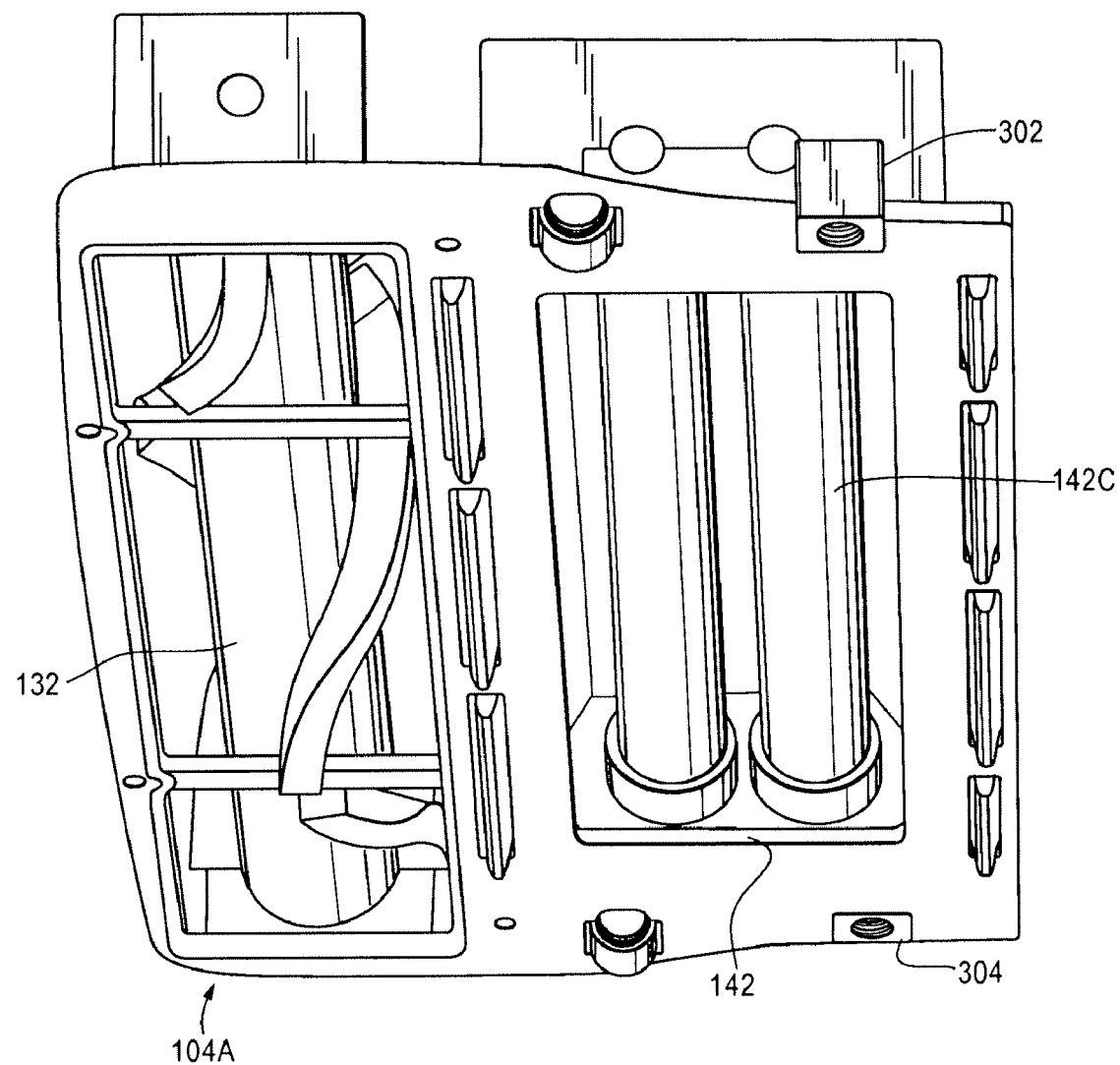
FIG. 13 illustrates a three-dimensional view of a portion of a disinfecting device provided in accordance with various embodiments of the invention.

In various embodiments, with reference to FIG. 13, one or more optical switches 302, 304 may be located in the base 104A of the main housing assembly 104 and/or in the light bulb assembly 142. As shown, the optical switches 302, 304 may be configured to determine when a surface of the base 104A of the device 102 is more than a predetermined distance from a surface of the cleaning medium. For example, the optical switches 302, 304 may be configured to deactivate the light bulb 142C when a predetermined detected distance between the optical switches 302, 304 and the cleaning medium is met or exceeded. In alternative embodiments, one or more mercury switches and/or one or more gravity switches may be employed in the device 102 to detect excessive tilt, slope, or other lifting of the device 102 with respect to the cleaning medium and to deactivate the light bulb 142C in accordance with the detected tilted or lifted condition. In various embodiments, the optical switches 302, 304 may work in conjunction with the safety switch 236 and the cleaning medium contact switch assemblies 250, 252, such that if any one or more of the optical switches 302, 304, the safety switch 236, or the cleaning medium contact switch assemblies 250, 252 is/are deactivated, then the light bulb 142C can be deactivated or not permitted to activate. As those skilled in the art will appreciate, this arrangement may be achieved, for example, by electrically connecting the safety switch 236, the cleaning medium contact switch assemblies 250, 252, and the optical switches 302, 304 in series in the device 102.

FIGS. 14A-C present front, side and top views of an embodiment of the invention. The device 102 can employ various arrangements of the features described above, including a safety switch 236, handle assembly 116, housing 104, light assembly 142 and cleaning assembly 132. Those of skill in the art will recognize that the device 102 may take various forms such as are common in cleaning devices.

In general, embodiments of the device 102 described herein can be structured to operate in various modes: such as vacuum only, which can be useful for substantially solid or substantially non-compressible cleaning media such as the surface of a hardwood floor, for example; or, vacuum with accompanying beater bar 132 rotation for various types of surfaces or floor coverings, such as carpeting or mattresses. In addition, the light bulb 142C may be on or off in either of these operational modes, radiating or not radiating UV light into the cleaning medium as desired during use of the device 102. In various embodiments, the device 102 may be configured for use primarily to perform disinfecting operations in association with UV light or UVC light radiated from the light bulb 142C. For example, such disinfecting operations may be performed with the device 102 as described above, with or without an accompanying vacuum cleaning operation capability, and/or with or without activation of the beater bar 132 or bulb-in-bar assembly 206 embodiments described herein.

It is to be understood that the figures and descriptions of the present invention have been simplified to illustrate elements that are relevant for a clear understanding of the present invention, while eliminating, for purposes of clarity, other elements. Those of ordinary skill in the art will recognize, however, that these and other elements may be desirable. However, because such elements are well known in the art, and because they do not facilitate a better understanding of the present invention, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the present invention, a single component may be replaced by multiple components, and multiple components may be replaced by a single component, to provide an element or structure or to perform a given function or functions. Except where such substitution would not be operative to practice certain embodiments of the present invention, such substitution is considered within the scope of the present invention.

The physical composition of various structural and functional components described herein may be comprised of different kinds of suitable materials. Examples of suitable materials that may be employed include, without limitation, polypropylene, polycarbonate, ABS plastic, polyethylene (e.g., HDPE), various elastomeric materials, and polytetrafluoroethylene ("PTFE").

The examples presented herein are intended to illustrate potential and specific implementations of the present invention. It can be appreciated that the examples are intended primarily for purposes of illustration of the invention for those skilled in the art. The diagrams depicted herein are provided by way of example. There may be variations to these diagrams or the operations described herein without departing from the spirit of the invention. For instance, in certain cases, method steps or operations may be performed in differing order, or operations may be added, deleted or modified.

Furthermore, whereas particular embodiments of the invention have been described herein for the purpose of illustrating the invention and not for the purpose of limiting the same, it will be appreciated by those of ordinary skill in the art that numerous variations of the details, materials and arrangement of elements, steps, structures, and/or parts may be made within the principle and scope of the invention without departing from the invention as described in the following claims.

The invention claimed is:

1. A device for disinfecting a cleaning medium comprising:
   an ultraviolet (UV) bulb positioned to radiate UV light onto the cleaning medium; and
   a lens disposed between the UV bulb and the cleaning medium, wherein the lens is adapted to be in direct contact with the cleaning medium.

2. A device as in claim 1 wherein the direct contact with the cleaning medium wipes the lens.

3. A device as in claim 1, further comprising:
   a housing for disposing the UV bulb and the lens; and
   wheels operatively associated with the housing.

4. A device as in claim 1, further comprising a lens frame for disposing the lens therein.

5. A device as in claim 4, wherein the lens frame is removable.

6. A device as in claim 4, wherein the lens frame is pivotably attached to the housing.

7. A device as in claim 1, wherein the lens allows greater then 80 percent transmittance of UV light irradiated from the UV bulb.

8. A device as in claim 1, wherein the lens is composed of fused silica or glass quartz.

9. A device as in claim 1, wherein the lens is no more than 3 millimeters thick.

10. A device as in claim 1, wherein the UV bulb is positioned about 2 inches above the cleaning medium.

11. A device as in claim 1, wherein the cleaning medium is exposed to a dosage of at least 30 milliJoules/centimeters of UV light during normal use.

12. A device as in claim 1, wherein the cleaning medium is exposed irradiance of at least 30 microwatts/centimeters$^2$.

13. A device as in claim 1, further comprising a bulb-in-bar assembly and wherein the UV bulb is positioned in the bulb-in-bar assembly.

14. A device as in claim 13, wherein the bulb assembly further comprises a reflector positioned to reflect UV light radiated from the UV bulb onto the cleaning medium.

15. A device as in claim 13, further comprising at least one fin extending from the bulb assembly and operable to transfer heat away from the bulb assembly.

16. A device as in claim 1, further comprising a vacuum assembly for vacuuming the cleaning medium.

17. A device for disinfecting a cleaning medium comprising:
- a UV light source positioned to radiate UV light onto the cleaning medium; and
- a lens disposed between the UV source and the cleaning medium, wherein the lens is adapted to be in direct contact with the cleaning medium, and wherein the direct contact with the cleaning medium wipes the lens.

18. A device for disinfecting a cleaning medium comprising:
- a housing;
- a UV light source disposed within the housing positioned to radiate UV light onto the cleaning medium;
- a lens disposed between the UV light source and the cleaning medium; and
- a vacuum assembly,
- wherein the lens is adapted to be in direct contact with the cleaning medium.

19. A device as in claim 18, wherein the vacuum assembly further comprises a beater bar.

20. A device as in claim 18, wherein the device is handheld.

* * * * *